(12) United States Patent
Saito et al.

(10) Patent No.: US 8,252,560 B2
(45) Date of Patent: Aug. 28, 2012

(54) PROCESS FOR PRODUCING USEFUL SUBSTANCE WITH IMMOBILIZED ENZYME

(75) Inventors: Jun Saito, Kamisu (JP); Yoshitaka Senda, Kamisu (JP); Keigo Hanaki, Kamisu (JP); Toshiteru Komatsu, Kamisu (JP)

(73) Assignee: Kao Corporation, Tokyo (JP)

( * ) Notice: Subject to any disclaimer, the term of this patent is extended or adjusted under 35 U.S.C. 154(b) by 393 days.

(21) Appl. No.: 12/518,285

(22) PCT Filed: Dec. 14, 2007

(86) PCT No.: PCT/JP2007/001403
§ 371 (c)(1),
(2), (4) Date: Jun. 9, 2009

(87) PCT Pub. No.: WO2008/072382
PCT Pub. Date: Jun. 19, 2008

(65) Prior Publication Data
US 2010/0041114 A1 Feb. 18, 2010

(30) Foreign Application Priority Data

Dec. 15, 2006 (JP) ................................. 2006-337889
Mar. 7, 2007 (JP) ................................. 2007-057541

(51) Int. Cl.
*C12P 7/64* (2006.01)
*C12N 11/00* (2006.01)
*C12N 11/14* (2006.01)

(52) U.S. Cl. .......................... 435/134; 435/174; 435/175
(58) Field of Classification Search .................. None
See application file for complete search history.

(56) References Cited

U.S. PATENT DOCUMENTS

| | | | |
|---|---|---|---|
| 4,629,742 A * | 12/1986 | Brady et al. ...................... 521/55 |
| 4,678,580 A | 7/1987 | Brady et al. | |
| 4,833,083 A * | 5/1989 | Saxena ........................... 435/403 |
| 5,010,004 A | 4/1991 | Kosugi et al. | |
| 6,190,624 B1 * | 2/2001 | Romatier ...................... 422/200 |
| 6,258,575 B1 * | 7/2001 | Shimizu et al. ............... 435/134 |
| 2003/0013165 A1 | 1/2003 | Komatsu et al. | |
| 2006/0292675 A1 | 12/2006 | Saito et al. | |
| 2009/0298142 A1 | 12/2009 | Saito et al. | |

FOREIGN PATENT DOCUMENTS

| | | |
|---|---|---|
| DE | 41 25 186 | 2/1993 |
| EP | 1 736 549 A1 | 12/2006 |
| JP | 61-85195 | 4/1986 |
| JP | 62-115283 | 5/1987 |
| JP | 62 179388 | 8/1987 |
| JP | 1-98494 | 4/1989 |
| JP | 9-508803 | 9/1997 |
| JP | 2000 160188 | 6/2000 |
| JP | 2000-160188 | 6/2000 |
| JP | 2003-00291 | 1/2003 |
| JP | 2007-125009 | 5/2007 |
| WO | 2007 043552 | 4/2007 |

OTHER PUBLICATIONS

Office Action issued Jul. 12, 2011 in Japan Application No. 2007-057541 (With English Translation).
Office Action issued Jul. 19, 2011 in Japan Application No. 2006-337889 (With English Translation).
Extended European Search Report issued Mar. 7, 2012, in Patent Application No. 07849833.4.
Office Action issued on May 22, 2012 for Japanese Patent Application No. 2006-337889 (with English Translation).

* cited by examiner

*Primary Examiner* — Chris R Tate
*Assistant Examiner* — Douglas F White
(74) *Attorney, Agent, or Firm* — Oblon, Spivak, McClelland, Maier & Neustadt, L.L.P.

(57) ABSTRACT

The present invention relates to a process for producing a fatty acid, which includes feeding a liquid mixture formed of two liquid phases that flow in a co-current manner into a fixed bed-type reaction column packed with immobilized lipase, and performing a hydrolysis reaction when the two liquid phases are in contact with the immobilized lipase in the fixed-bed reaction column; wherein the fixed-bed reaction column comprises partition plates so as to comprise a plurality of tube-shaped structures, wherein each tube-shaped structure has a cross-section which is rectangular, circular, oval, or polygonal in shape with at least a part being unclosed and the cross-section has a representative length of 100 mm or less.

8 Claims, 4 Drawing Sheets

PROCESS FOR PRODUCING USEFUL SUBSTANCE WITH IMMOBILIZED ENZYME

FIELD OF THE INVENTION

The present invention relates to a process for producing a useful substance by a reaction using a fixed bed-type reaction column packed with an immobilized enzyme.

BACKGROUND OF THE INVENTION

As the reaction which is carried out by passing a liquid through a fixed bed-type reaction column, there are known reactions utilizing an immobilized enzyme, which are used in the production of L-aspartic acid, production of transesterified oils and fats, hydrolysis of lactose, hydrolysis of oils and fats, and the like. These reactions are normally carried out by use of the simplest drum type reactor, because their heating values are relatively small.

Among the reactions utilizing an immobilized enzyme, in the case of allowing two or more kinds of liquids to flow through the reactor as in the case of the hydrolysis of oils and fats, it is preferable to pass the reaction liquids in a uniformly mixed state, from the viewpoint of enhancing the reaction efficiency. In this case, the oil phase substrate and the aqueous phase substrate used in the hydrolysis do not become a single phase, even if mixed, so it is common for this mixture to become an emulsion. On the other hand, it is difficult for emulsion particles to reach the enzyme which is adsorbed to the interior of pores of the support, so there has been a technology which allows the rate of liquid passage not to exceed an extent to which the reaction liquids are not emulsified (see Patent Document 1).

Furthermore, as the process of allowing an oil phase substrate and an aqueous phase substrate to flow through a fixed bed, there maybe mentioned processes of allowing the substrates to flow in a countercurrent manner (see Patent Documents 1 and 2), and processes of allowing the substrates to flow in a co-current manner (see Patent Document 3). However, the former processes require special structures and operating processes, so it is common to make use of a method allowing the substrates to flow in a co-current manner.
[Patent Document 1] JP-A-61-85195
[Patent Document 2] JP-A-01-98494
[Patent Document 3] JP-A-2000-160188

DISCLOSURE OF THE INVENTION

The present invention provides a process for producing a useful substance, which include feeding a liquid mixture formed of two liquid phases into a fixed bed-type reaction column packed with an immobilized enzyme, and performing a reaction while allowing the liquid mixture to flow in the same direction in a co-current manner, wherein the fixed bed-type reaction column has partition plates inserted in the longitudinal direction of the fixed bed-type reaction column so as to form a plurality of tube-shaped structures, wherein each tube-shaped structure has a lateral cross-section which is circular or polygonal in shape with at least a part being unclosed and has a representative length of 100 mm or less, and wherein the immobilized enzyme is packed into the tube-shaped structures, and wherein the liquid mixture is fed into the tube-shaped structures.

The present invention also provides a process for producing a useful substance, which includes feeding a liquid mixture formed of two liquid phases into a fixed bed-type reaction column having a column diameter of 35 mmφ or larger and packed with an immobilized enzyme, and performing a reaction while allowing the liquid mixture to flow in the same direction in a co-current manner, wherein a fixed bed-type reaction column which is packed with an immobilized enzyme such that the ratio of the column diameter (mm) of the fixed bed-type reaction column to the average particle size (mm) of the immobilized enzyme (column diameter/average particle size) is 135 (mm/mm) or less, is used as the fixed bed-type reaction column.

BRIEF DESCRIPTION OF THE DRAWINGS

FIG. 4(a) is a diagram showing the partition plates having slits for combination.

DETAILED DESCRIPTION OF THE INVENTION

Figure 1:
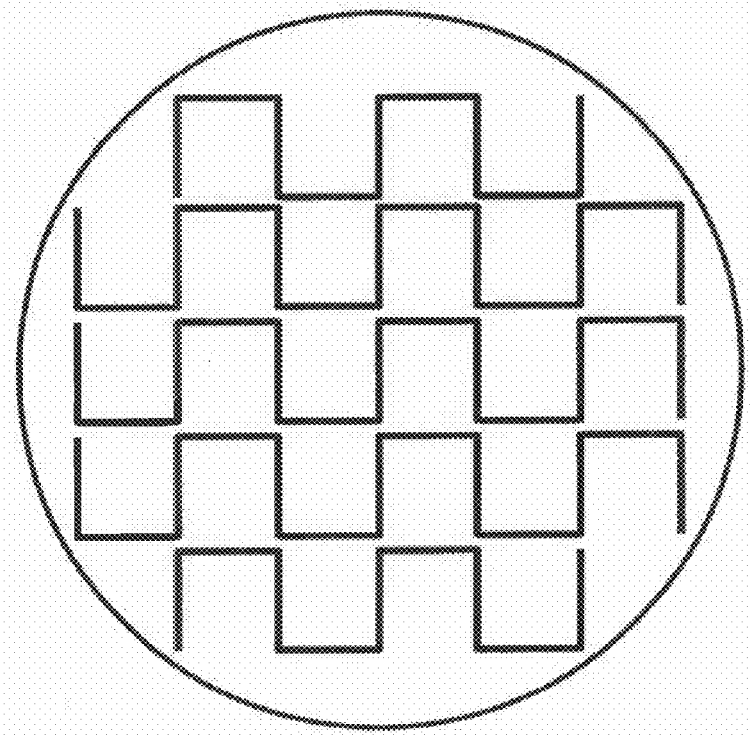
FIG. 1 is a diagram showing the lateral cross-section of an enzyme column mounted with concavo-convex type partition plates.

In the above-described process of performing a reaction by passing a liquid mixture formed of two liquid phases into a fixed bed-type reaction column packed with an immobilized enzyme, particularly in the case of allowing the liquid mixture to flow without being emulsified, it was found that as the diameter of the reaction column is increased, the flow of the reaction liquid inside the column becomes non-uniform, some of the reactions do not work well, and the activity of enzyme weakens, eventually leading to a problem of decreased reactivity. In this case, if it is simply attempted to lengthen the time of contact between the immobilized enzyme and the reaction liquid in order to increase the reactivity, there is also a problem in which productivity (flow rate) decreases.

Therefore, the present invention relates to a process for producing a useful substance by allowing a liquid mixture formed of two liquid phases to flow through a fixed bed-type reaction column packed with an immobilized enzyme to perform a reaction, in which the useful substance is more efficiently produced by increasing reactivity without decreasing the flow rate, and thereby enhancing productivity.

Thus, the inventors of the present invention analyzed the characteristics of the passage of the reaction liquid in a fixed bed-type reaction column packed with an immobilized enzyme, and as a result, they found that as the cross-sectional area of the flow channel is smaller, the flow of the reaction liquid becomes uniform, and reactivity is enhanced. Thus the inventors found that, when partition plates are inserted inside a fixed bed-type reaction column packed with an immobilized enzyme and having a large cross-sectional area, in the longitudinal direction of the fixed bed-type reaction column so as to form a plurality of tube-shaped structures, each tube-shaped structure having a lateral cross-section which is circular or polygonal in shape with at least a part being unclosed and has a representative length of 100 mm or less, and an enzymatic reaction is performed within each of the tube-shaped structures having a small cross-sectional area, productivity can be enhanced while maintaining high reactivity.

Furthermore, the inventors of the present invention conducted various investigations on the activity appeared by an enzyme in a fixed bed-type reaction column packed with an immobilized enzyme, and found that in the case of using a reaction column having a large column diameter, when the ratio of the column diameter of the reaction column and the particle size of the immobilized enzyme is defined, the enzymatic activity can be effectively appeared, and thus productivity can be enhanced while maintaining high reactivity.

In the case of using an immobilized enzyme, if it is intended to enhance the activity appeared by the enzyme, a person ordinarily skilled in the art would reduce the particle size of the support in order to enlarge the specific surface area of the support. Although the current technique is effective in the case where the column diameter of the fixed bed-type reaction column is small, it has been found surprisingly that if the column diameter is made large, no sufficient effect takes place unless an opposite means is employed with respect to the support particle size.

According to the present invention, even when a reaction column having a large column diameter is used in the reaction performed by feeding a liquid mixture formed of two liquid phases into a fixed bed-type reaction column packed with an immobilized enzyme, it is possible not only to make the flow of the whole reaction liquid inside the column uniform, but also to lead to the effective appearing of the enzymatic activity. As a result, reactivity and productivity can be enhanced. Particularly, in the hydrolysis of oils and fats, the enzymatic activity can be effectively appeared, and thus fatty acids can be efficiently produced. Furthermore, the operability at the time of removing the immobilized enzyme packed in the reaction column is good.

In the present invention, a liquid mixture formed of two liquid phases is fed into a fixed bed-type reaction column packed with an immobilized enzyme. The fixed bed-type reaction column (hereinafter, also referred to as "enzyme column") is meant by that an immobilized enzyme is packed in a column or the like, so that the reaction liquid can be made to flow through the gaps between supports of immobilized enzyme, and through the pores of the support of immobilized enzyme. The term "two liquid phases" means the state in which two types of liquids do not form a single phase even after mixing, and the state of being phase separated, the term includes a uniform state as well as an emulsified state.

According to an aspect of the present invention, the process is preferably a process for producing fatty acids as the useful substance by a hydrolysis reaction of oils and fats, in which an oil and fat splitting enzyme adsorbed onto an support is used as the immobilized enzyme, and as the two liquid phases, an oil phase substrate and an aqueous phase substrate are allowed to flow through an reaction column packed with the oil and fat splitting enzyme.

In the present invention, the two liquid phases are allowed to flow in the same direction in a co-current manner. In this case, the two liquid phases may be mixed in advance and supplied in an emulsified state, or may also be supplied in the form of separated phases. Furthermore, the two liquid phases may also be supplied alternately at an interval of a predetermined time period. The supply of the respective substrates into the enzyme column may be carried out in a downward flow from the top of the column to the bottom of the column, or may also be carried out in an upward flow from the bottom of the column to the top of the column.

The immobilized enzyme used in the present invention is an enzyme supported on a support by adsorption or the like.

As for the support, there may be mentioned inorganic supports such as celite, diatomaceous earth, kaolinite, silica gel, molecular sieves, porous glass, activated carbon, calcium carbonate, and ceramics; organic polymers such as ceramic powders, polyvinyl alcohol, polypropylene, chitosan, ion exchange resins, hydrophobic adsorption resins, chelating resins and synthetic adsorption resins; and the like. Particularly from the viewpoint of having high water retaining power, ion exchange resins are preferred. Furthermore, among the ion exchange resins, porous resins are preferred from the viewpoint that the large surface area of the porous resins can increase the amount of adsorption of the enzyme.

The particle size of the resin used as the support is preferably 0.1 to 10 mm, more preferably 0.2 to 6 mm, even more preferably 0.25 to 4 mm, and far more preferably 0.3 to 2 mm. The pore size is preferably 10 to 150 nm, and more preferably 10 to 100nm. As for the material, there may be mentioned phenol formaldehyde-based, polystyrene-based, acrylamide-based, divinylbenzene-based resins and the like, and in particular, phenol formaldehyde-based resins (for example, Duolite A-568 manufactured by Rohm and Haas Company) are preferred from the viewpoint of enzyme adsorptivity.

The enzyme used for the immobilized enzyme of the present invention is not particularly limited, but from the viewpoint of having a large effect of enhancing productivity, lipases as the enzymes for splitting oils and fats are preferred. The lipases that can be used may be animal-derived and plant-derived lipases, as well as commercially available, microorganism-derived lipases. As for the microorganism-derived lipases, there may be mentioned those originating from genus *Rhizopus*, genus *Aspergillus*, genus *Mucor*, genus *Pseudomonas*, genus *Geotrichum*, genus *Penicillium*, genus *Candida*, and the like.

The temperature for carrying out immobilization of an enzyme can be determined based on the properties of the enzyme, and is preferably 0 to 60° C., and more preferably 5 to 40° C., where deactivation of an enzyme does not occur. Furthermore, the pH of the enzyme solution used at the time of immobilization may be within a range where denaturation of the enzyme does not occur, and can be determined based on the properties of the enzyme as in the case of temperature, but is preferably pH 3 to 9. In order to maintain this pH, a buffer solution is used, and examples of the buffer solution include acetate buffer solution, phosphate buffer solution, Tris-hydrochloric acid buffer solution, and the like. The enzyme concentration in the enzyme solution is preferably a concentration which is equal to or less than the saturation solubility of the enzyme, while being sufficient, from the viewpoint of immobilization efficiency. As for the enzyme solution, a supernatant obtained after removing the insoluble part by centrifugation as necessary, or a solution purified by ultrafiltration or the like, can also be used. The mass of enzyme used may vary depending on the activity of that enzyme, but is preferably 5 to 1000% by mass, and more preferably 10 to 500% by mass, based on the mass of support.

In the case of immobilizing an enzyme, and the enzyme may be directly adsorbed on the support, but in order to obtain an adsorption state which is likely to appear high activity, it is preferable to treat the support in advance with a fat-soluble fatty acid or a derivative thereof, before adsorbing the enzyme. As for the method of contacting a fat-soluble fatty acid or a derivative thereof with the support, these materials may be directly added into water or an organic solvent; however, to make the dispersibility good, the fat-soluble fatty acid or the derivative thereof may be first dispersed and dissolved in an organic solvent, and then the solution may be added to the support which has been dispersed in water. As for this organic solvent, chloroform, hexane, ethanol and the like may be mentioned. The mass of use of the fat-soluble fatty acid or a derivative thereof is preferably 1 to 500% by mass, and more preferably 10 to 200% by mass, based on the mass of support. The contacting temperature is preferably 0 to 100° C., and more preferably 20 to 60° C., and the contacting time is preferably about 5 minutes to 5 hours. The support which has undergone this treatment is filtered and recovered, and may also be dried. The drying temperature is preferably room temperature to 100° C., and drying under reduced pressure may also be performed.

Among the fat-soluble fatty acids or derivatives thereof for treating the support in advance, there may be mentioned, as for the fat-soluble fatty acids, saturated or unsaturated, linear or branched fatty acids having 4 to 24 carbon atoms, and preferably 8 to 18 carbon atoms, which may have a hydroxyl group. Specific examples thereof include capric acid, lauric acid, myristic acid, oleic acid, linolic acid, α-linolenic acid, ricinolic acid, isostearic acid and the like. Furthermore, as the derivatives of the fat-soluble fatty acids, there may be mentioned esters of these fat-soluble fatty acids and monohydric or polyhydric alcohols or sugars, phospholipids, products obtained by adding ethylene oxide to these esters, and the like. Specific examples thereof include methyl esters, ethyl esters, monoglycerides and diglycerides of the aforementioned fatty acids, ethylene oxide adducts thereof, polyglycerin esters, sorbitan esters, sucrose esters thereof, and the like. It is preferable that these fat-soluble fatty acids and derivatives thereof are all in the liquid state at normal temperature, in view of the process of immobilizing an enzyme on a support. These fat-soluble fatty acids or derivatives thereof may be used in combination of two or more species, and naturally occurring fatty acids such as rapeseed fatty acids and soybean fatty acids can also be used.

The hydrolytic activity of the immobilized enzyme is preferably 20 U/g or greater, more preferably 100 to 10000 U/g, and more preferably in the range of 500 to 5000 U/g. Here, 1 U of the enzyme indicates the capacity of the enzyme which produces 1 μmol of free fatty acids in one minute when a mixed liquid of oils and fats:water=100:25 (mass ratio) is subjected to hydrolysis for 30 minutes at 40° C., while stirring and mixing the mixed liquid. The hydrolytic activity of the immobilized enzyme (U/g-oil) imparted per unit mass of the oils and fats, and the time taken to reach a certain rate of hydrolysis are in an approximately inversely proportional relationship.

In the case of performing hydrolysis by using a packed bed (enzyme column) packed with an immobilized enzyme, the rate of hydrolysis may vary with the conditions for liquid supply (rate of liquid passage, temperature, and the like), and from the rate of hydrolysis of the oils and fats at the outlet of the enzyme packed bed, the time taken by hydrolysis (retention time in the packed bed), the mass of oils and fats present in the packed bed (g-oil), and the packing mass of the immobilized enzyme (g), the apparent activity (appeared activity) (U/g) of the immobilized enzyme is determined. In addition, in order to determine the mass of oils and fats present in the packed bed, the mass is determined by multiplying the volume of the immobilized enzyme packing unit, with the porosity of the packing unit, the volume ratio of the oils and fats in the reaction liquid, and the specific gravity of the oils and fats.

One preferable species in the liquid mixture which forms two liquid phases according to the present invention, is an oil phase substrate. The oil phase substrate refers mainly to plant oils, animal oils, or oils and fats combining these, but the oils and fats may also contain triacylglycerols, as well as diacylglycerols, monoacylglycerols or fatty acids, or may also contain fatty acids obtainable as a result of hydrolysis. Specific examples of the oil phase substrate include plant oils such as rapeseed oil, soybean oil, sunflower oil, palm oil and linseed oil; animal oils such as beef tallow, pork fats and fish oil; and the like, or oils and fats in combination of these. In regard to these oils and fats, deodorized oil, as well as undeodorized oils and fats which have not been deodorized in advance can be used, but it is preferable to use undeodorized oil and fat for part or all of these oils and fats, from the viewpoint of reducing trans unsaturated fatty acids and conjugated unsaturated fatty acids, so as to allow plant sterols, plant sterol fatty acid esters, and tocopherols derived from the raw material oils and fats to remain. In the oil phase substrate, oil-soluble components such as fatty acids other than the aforementioned oils and fats may also be mixed in. The fatty acids also refer to those containing one or more of the aforementioned glycerides, in addition to the fatty acids obtainable as a result of hydrolysis.

One preferable species in the liquid mixture which forms two liquid phases according to the present invention, is an aqueous phase substrate. The aqueous phase substrate is water, but the substrate may also have other water-soluble components mixed therein, such as glycerin which is obtainable as a result of hydrolysis.

It will be preferable for the fixed bed-type reaction column (enzyme column) used in the present invention, to have a shape which can withstand the pressing force of the pump used. Furthermore, it is preferable that a jacket is provided around the enzyme column so as to adjust the reaction liquid flowing through inside the enzyme column to a temperature appropriate for the enzyme reaction.

The temperature in the enzyme column is preferably set at 0 to 60° C., and more preferably 20 to 40° C., to induce the activity of the immobilized enzyme more effectively.

The length of the enzyme column may be any length necessary for obtaining a desired rate of hydrolysis, but from the viewpoints of reactivity, loss of the pressure inside the column, and the like, the length is preferably in the range of 0.01 to 10 m, and preferably 0.1 to 5 m.

In the present invention, partition plates are inserted in the enzyme column in longitudinal direction of the enzyme column so as to form a plurality of tube-shaped structures, each tube having a lateral cross-section which is circular or polygonal in shape with at least a part being unclosed and has a representative length of 100 mm or less, and an immobilized enzyme is packed in the tube-shaped structures, while the liquid mixture is supplied into the tube-shaped structures to perform a reaction. When a reaction is performed within a plurality of tube-shaped structures having such small cross-sectional areas, the cross-sectional area of the flow channel inside the enzyme column is decreased, and the flow of the reaction liquid which forms two liquid phases can be made uniform. Furthermore, when tube-shaped structures are formed, with each tube having at least a part of the lateral cross-section being unclosed, the volume ratio of the immobilized enzyme packing unit is increased, reactivity is increased, and cost reduction can also be attempted. Furthermore, the operability of removal of the immobilized enzyme is good. Here, in this case, if there are gaps between the partition plates and the inner wall of the enzyme column, it is preferable to pack these gaps with the immobilized enzyme, in view of making the flow of the reaction liquid uniform. Also, the term "representative length" in the present invention means the length of the diagonal if the lateral cross-section is rectangular; if the lateral cross-section is circular, the diameter; and if the lateral cross-section is oval, polygonal or the like, the diameter of a circle having the same area as the projected area of such a shape.

Figure 2:
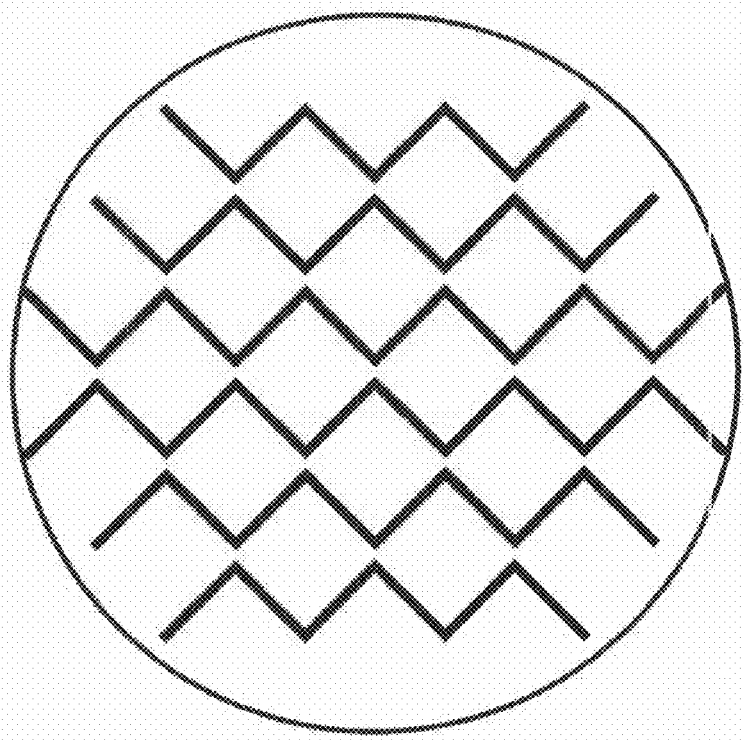
FIG. 2 is a diagram showing the lateral cross-section of an enzyme column mounted with zigzag-shaped partition plates.
Figure 3:
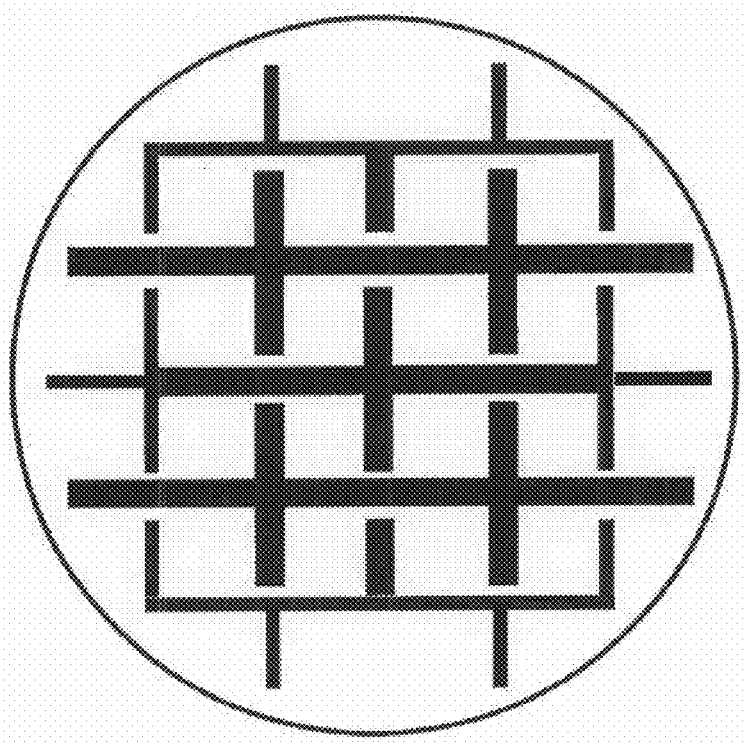
FIG. 3 is a diagram showing the lateral cross-section of an enzyme column, in which the interior of a polygonal shape formed by mounting concave type partition plates, is partitioned with partition plates having different plate shapes.
Figure 4:
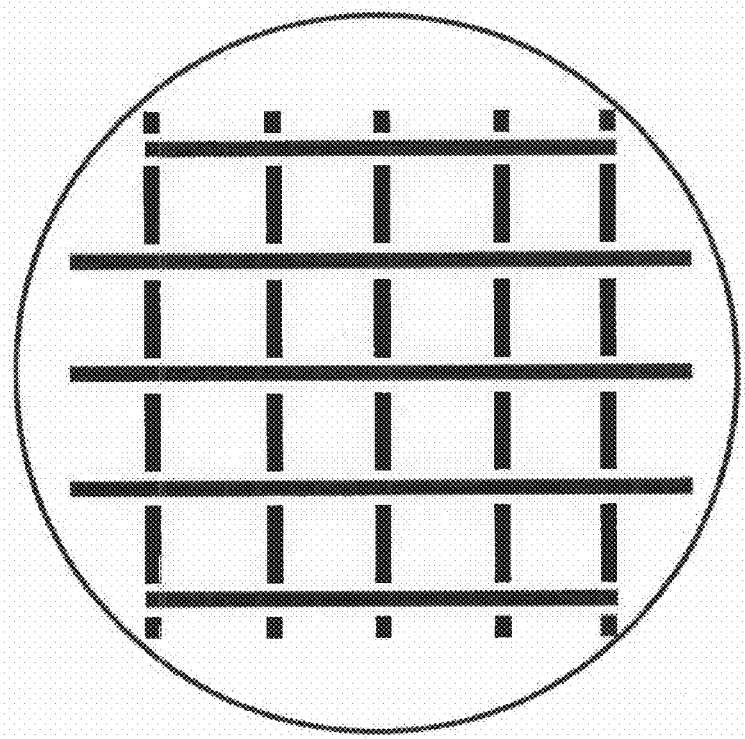
FIG. 4 is a diagram showing the lateral cross-section of an enzyme column in which partition plates having slits for combination are mounted in combination.
Figure 4:
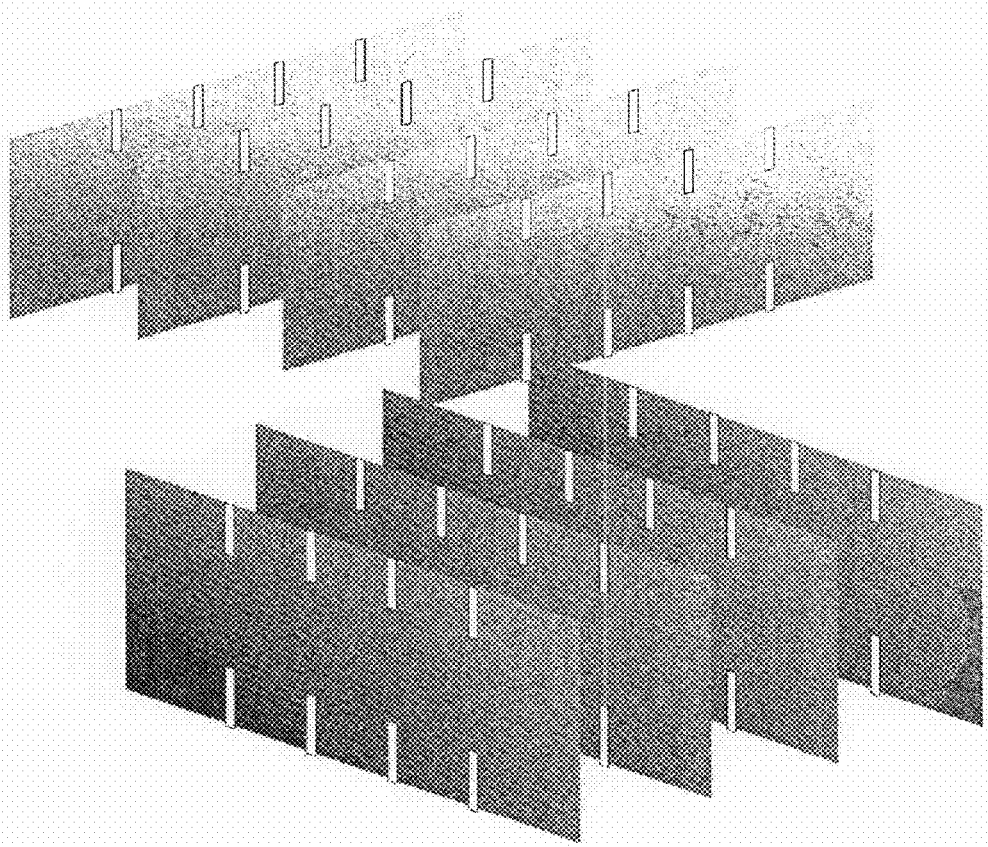

It is preferable to insert the partition plates in the longitudinal direction so that a plurality of tube-shaped structures having the above-mentioned cross-sectional areas can be formed in the enzyme column. For example, there may be mentioned a method of mounting concavo-convex type partition plates (flat plate, corrugated plates, and the like) inside the enzyme column (FIG. 1); a method of mounting zigzag-shaped partition plates (FIG. 2); a method of partitioning the interior of a polygonal shape which is formed by mounting concave type partition plates, with other partition plates (FIG. 3); a method of combining a plurality of partition plates (FIG. 4(a)) having slits for combination (FIG. 4); and the like. There may also be mentioned a method of mounting wave-shaped partition plates; a method of partitioning the interior of a circular shape which is formed by mounting wave-shaped partition plates, with other partition plates; a method of mounting a plurality of curve-shaped or plate-shaped partition plates in combination, to form a circular shape or a polygonal shape; and the like. The shape of the lateral cross-section of the tube is, in the case of a polygonal shape, preferably a regular triangular shape, a square shape or a regular hexagonal shape, and in the case of a circular shape, a circular shape or an oval shape, from the viewpoint of the efficiency of mounting partition plates.

The representative length of the lateral cross-section of each tube-shaped structure (one flow channel) of the plurality of tube-shaped structures formed by the partition plates, is 100 mm or less, and from the viewpoint of enhancing the reactivity, it is preferable to have a representative length of 75 mm or less, more preferably 50 mm or less, and even more preferably 35 mm or less.

The length of the unclosed part in the circular-shaped or polygonal-shaped lateral cross-section is preferably 0.1 to 10 mm, more preferably 0.5 to 8 mm, and even more preferably 1 to 6 mm, from the viewpoint of enhancing the reactivity. Here, spacers may also be partially inserted in order to maintain the gap between a partition plate and another partition plate to be constant. Furthermore, in the case of the above-described partition plates having slits for combination, it is preferable to set the width of the slits to be wider than the thickness of the partition plates by 0.2 to 20 mm, more preferably 1 to 16 mm, and even more preferably 2 to 12 mm.

Figure 5:
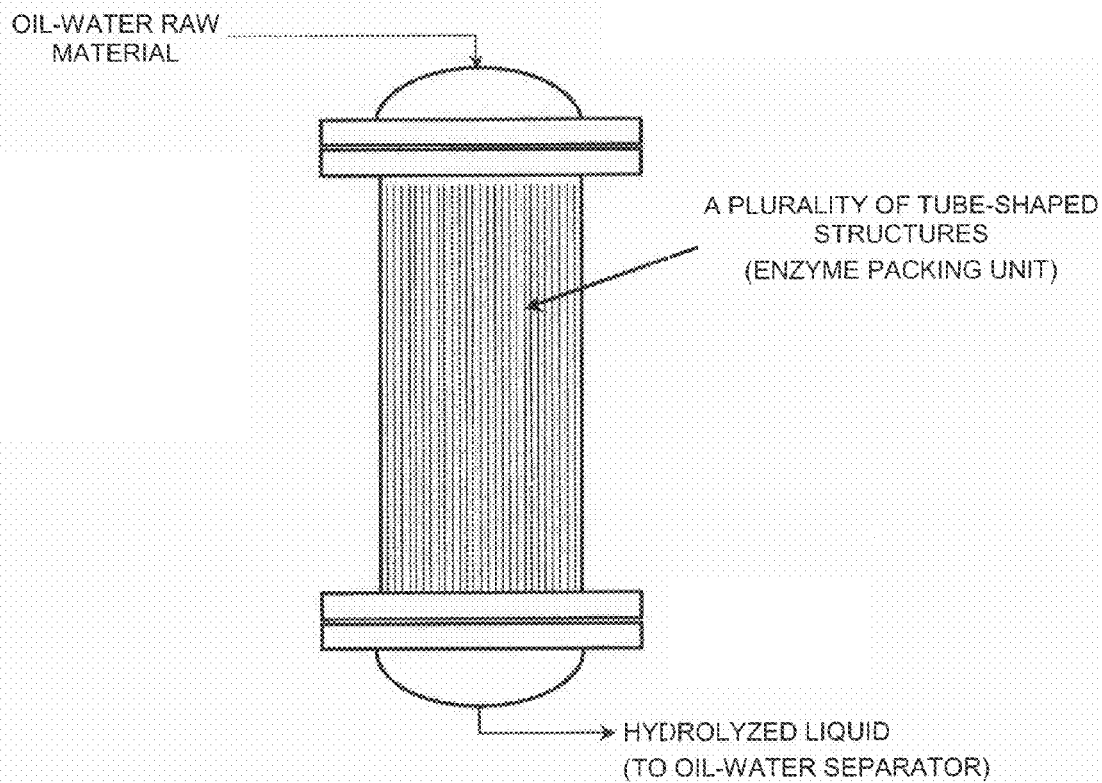
FIG. 5 is a conceptual diagram showing the flow of the reaction liquid in the enzyme column.

The immobilized enzyme is packed in the tube-shaped structures formed by the mounting of partition plates in the enzyme column, and the liquid mixture of two liquid phases (reaction liquid) is supplied into the tube-shaped structures (see FIG. 5).

By partitioning, the flow of the liquid mixture of two liquid phases (reaction liquid) in the enzyme column becomes uniform.

When the immobilized enzyme is packed, if there are gaps between the partition plates and the inner wall of the enzyme column and the gaps are extremely narrow, it becomes difficult to pack the immobilized enzyme. If the packing into these gaps is insufficient, the packing in the entire enzyme column becomes non-uniform, and a decrease in the volumetric density may occur. In this case, the flow of the reaction liquid becomes non-uniform and may serve as a cause which brings a decrease in the reaction efficiency. Therefore, it is preferable to set the gaps between the partition plates and the inner wall of the enzyme column to a certain value or above. The size of the gap depends on the type or particle size of the packing material such as immobilized enzyme, and the size of the partition plate, and it is preferable to set the narrowest part of the gap between a partition plate and the inner wall of the enzyme column to 1 mm or larger, and more preferably to 5 mm or larger, in view of packing the immobilized enzyme uniformly without any voids. It is preferable to set the upper limit of the gap to be equal to or less than the representative length of the cross-section of one tube, from the viewpoint of making the flow of the reaction liquid uniform, and it is more preferable to set the upper limit to 70 mm or less, and even more preferably 50 mm or less.

It is preferable that the length of a partition plate in the enzyme column is equal to or larger than the packing thickness of the immobilized enzyme, in view of making the flow of the whole reaction liquid in the column uniform, but even though the length is shorter than the packing thickness, if the length is in the range of 50% or larger, and 75% or larger, of the packing thickness, the same effects are obtained.

Furthermore, the partition plates may not have breaks along the entire length, but from the viewpoint of operability such as the ease of exchanging the packed immobilized enzyme, it is preferable that the partition plates are divided in multiple stages in the vertical direction. The number of stages depends on the total length of the enzyme column, but is preferably 2 to 30 divisions, and more preferably 2 to 10 divisions. Furthermore, the partition plates on each stage may be respectively divided into multiple parts in the lateral direction, or may be unitized in every compartment, in view of the ease of mounting in the enzyme column.

Furthermore, according to the present invention, in the case where the reaction is performed by using an enzyme column having a column diameter of 35 mmφ or larger, it is preferable to set the ratio of the column diameter (mm) to the average particle size (mm) of the immobilized enzyme (column diameter/average particle size), to 135 (mm/mm) or less. If the column diameter of the enzyme column is less than 35 mmφ, a decrease in the enzymatic activity is not likely to occur, and reactivity is also good. However, as the diameter of the enzyme column is increased beyond 35 mmφ, the activity appeared by the enzyme tends to decrease, and as a result, reactivity may undergo a decrease. Also in the case of using an enzyme column having a large column diameter, when the ratio of the column diameter of the enzyme column and the average particle size of the immobilized enzyme is defined, scaling up becomes possible, and at the same time, a decrease in the activity of the enzyme can be prevented, so that the useful substance can be efficiently produced.

It is preferable to have the column diameter/average particle size to be 5 to 135 (mm/mm), more preferably 15 to 130 (mm/mm), and even more preferably 30 to 125 (mm/mm), from the viewpoint of enhancing the reactivity. Here, according to the present invention, the average particle size of the immobilized enzyme obtained by supporting an enzyme refers to the value measured by a laser scattering diffraction particle size distribution analyzer LS13320 (manufactured by Beckman Coulter, Inc.).

It is preferable to set the column diameter of the enzyme column to be 35 to 1000 mmφ, more preferably 35 to 800 mmφ, even more preferably 40 to 600 mmφ, and far more preferably 50 to 300 mmφ, from the viewpoints of operability such as the ease of packing of the immobilized enzyme, reactivity and productivity.

In regard to the method of supplying the reaction liquid to the enzyme column, the phases may be respectively supplied through pipes which are separately connected directly to the enzyme column, or the supply may be conducted through a commonly shared pipe. However, from the viewpoints of avoiding emulsification of the aqueous phase and the oil phase, and of operability, it is preferable to supply the phases separately through pipes which are connected directly to the enzyme column.

It is preferable to set the linear velocity of liquid passage of the reaction liquid at 1 to 400 mm/min, and more preferably 5 to 200 mm/min. This linear velocity of liquid passage (mm/min) means a value expressed as a quotient of the amount of liquid transfer per minute (mm$^3$/min) (or also referred to as the velocity of liquid transfer ($10^{-3}$ mL/min)), divided by the cross-sectional area of the packed bed (mm$^2$). As the pressure inside the packed column increases as a result of increasing the linear velocity of liquid passage, liquid passage becomes difficult, and an enzyme packed column having high pressure resistance is required, and also, there may occur situations in which the immobilized enzyme is crushed due to the increase in the pressure inside the column. Therefore, it is preferable to set the linear velocity of liquid passage at 400 mm/min or less. Furthermore, it is preferable to set the linear velocity of liquid passage at 1 mm/min or greater, from the viewpoint of productivity. Since the activity appeared by the immobilized enzyme changes with the linear velocity of liquid passage, a reaction appropriate for the desired production capacity and manufacturing costs can be carried out by selecting the optimum linear velocity of liquid passage and thereby determining the reaction conditions.

The retention time of the reaction liquid in the enzyme column is preferably 30 seconds to 120 minutes, and more preferably 1 minute to 80 minutes, in view of avoiding the equilibrium state of the hydrolysis reaction, more effectively eliciting the activity of the immobilized enzyme, and enhancing the productivity. The retention time (min) is expressed as the value obtained by multiplying the thickness (mm) of the packed bed with the porosity, and dividing this product by the linear velocity of liquid passage (mm/min).

In the present invention, from the viewpoint of good balance between reactivity, productivity and the like, the reaction liquid which passed through the enzyme column may be directly used as the completed reaction product. Alternatively, the process may be carried out such that the reaction liquid is first subjected to oil-water separation, fresh water is added after the oil phase is subjected to fractionation, and the mixture is supplied again into the same enzyme column by the same method as described above, and the reaction liquid may be repeatedly passed until the desired reaction ratio is obtained. Furthermore, the process may also be carried out such that the reaction liquid is first subjected to oil-water separation, the oil phase is subjected to fractionation, fresh water is added, and the mixture is supplied again into another enzyme column by the same method as described above, to thus perform a continuous reaction. The process may also be carried out by a pseudo-countercurrent method in which an oil phase having a higher rate of degradation is reacted with a fresh aqueous phase, by using a plurality of enzyme columns, and while performing oil-water separation of the reaction liquid, supplying the oil phase into the subsequent enzyme column and supplying the aqueous phase into the previous enzyme column. As for the oil-water separation method for the reaction liquid, oil-water separators of spontaneously settling type, centrifuging type and the like are generally used, but are not particularly limited.

EXAMPLES

[Preparation of Immobilized Enzyme (1)]

1 part by weight of Duolite A-568 (manufactured by Rohm and Haas Company, particle size distribution 100 to 1000 µm) was stirred for one hour in 10 parts by mass of a 1/10 N NaOH solution. After filtering, the mixture was washed with 10 parts by mass of ion exchanged water, and pH equilibration was carried out with 10 parts by mass of a 500 mM acetic buffer solution (pH 7). Thereafter, pH equilibration was carried out twice for two hours each, with 10 parts by mass of a 50 mM acetic buffer solution (pH 7). Subsequently, filtration was performed to recover the support, and then ethanol substitution was performed for 30 minutes with 5 parts by mass of ethanol. After filtering the resultant, 5 parts by mass of ethanol containing 1 part by mass of ricinolic acid was added, and ricinolic acid was adsorbed onto the support for 30 minutes. After recovering the support by filtration, the support was washed four times for 30 minutes each, with 5 parts by mass of a 50 mM acetic buffer solution (pH 7), ethanol was removed, and the support was recovered by filtration. Subsequently, the support was contacted for 5 hours with an enzyme solution in which 1 part by mass of a commercially available lipase (Lipase AY, Amano Pharmaceutical Co., Ltd.) was dissolved in 9 parts by mass of a 50 mM acetic buffer solution (pH 7), to perform immobilization. The resultant was filtered, and the immobilized enzyme was recovered and washed with 10 parts by mass of a 50 mM acetic buffer solution (pH 7), to remove any unimmobilized enzymes or proteins. Subsequently, 4 parts by mass of rapeseed oil which actually performs degradation was added, and the mixture was stirred for 12 hours. The above-described operation was all performed at 20° C. Thereafter, the immobilized enzyme was separated from the oil and fat by filtration, and was used as the immobilized enzyme. As a result, there was obtained an immobilized lipase which exhibited a hydrolytic activity (activity that should be appeared) of 2700 U/g (dry weight). The average mass-based particle size of the immobilized enzyme was 451 µm.

[Preparation of Immobilized Enzyme (2)]

1 part by mass of Duolite A-568 (manufactured by Rohm and Haas Company, particle size distribution 100 to 1000 µm) was stirred for one hour in 10 parts by mass of a 1/10 N NaOH solution. After filtering, the mixture was washed with 10 parts by mass of ion exchanged water, and pH equilibration was carried out with 10 parts by mass of a 500 mM acetic buffer solution (pH 7). Thereafter, pH equilibration was carried out twice for two hours each, with 10 parts by mass of a 50 mM acetic buffer solution (pH 7). Subsequently, filtration was performed to recover the support, and then ethanol substitution was performed for 30 minutes with 5 parts by mass of ethanol. After filtering the resultant, 5 parts by mass of ethanol containing 1 part by mass of ricinolic acid was added, and ricinolic acid was adsorbed onto the support for 30 minutes. After recovering the support by filtration, the support was washed for four times for 30 minutes each, with 5 parts by mass of a 50 mM acetic buffer solution (pH 7), ethanol was removed, and the support was recovered by filtration. Subsequently, the support was contacted for 5 hours with an enzyme solution in which 1 part by mass of a commercially available lipase (Lipase AY, Amano Pharmaceutical Co., Ltd.) was dissolved in 9 parts by mass of a 50 mM acetic buffer solution (pH 7), to perform immobilization. The resultant was filtered, and the immobilized enzyme was recovered and washed with 10 parts by mass of a 50 mM acetic buffer solution (pH 7), to remove any unimmobilized enzymes or proteins. Subsequently, 4 parts by mass of soybean oil which actually performs degradation was added, and the mixture was stirred for 12 hours. The above-described operation was all performed at 20° C. Thereafter, the immobilized enzyme was separated from the oil and fat by filtration, and was used as the immobilized enzyme (hereinafter, indicated as immobilized enzyme A). Furthermore, an support obtained by pulverizing Duolite A-568 and classifying the product, and an support obtained by classifying Duolite A-568 and removing microparticles having a size of 425 µm or less were used to prepare immobilized enzymes by the same method as described above (respectively designated as immobilized enzyme B and immobilized enzyme C). The hydrolytic activity (activity to be appeared) and the average mass-based particle sizes of the immobilized enzymes A to C are presented in Table 1.

TABLE 1

|  | Hydrolytic activity [U/g] | Average particle size (mass-based) [µm] |
|---|---|---|
| Immobilized enzyme A | 2400 | 500 |
| Immobilized enzyme B | 3030 | 300 |
| Immobilized enzyme C | 2150 | 580 |

Example 1

In a column (inner diameter 70 mm, height 1500 mm) made of stainless steel equipped with a jacket, in which zigzag-shaped partition plates (equivalent to FIG. 2, thickness 1 mm, height 1300 mm) having a lateral cross-section which was rectangular in shape with a size of 11.4 mm×11.4 mm (representative length 16 mm), were mounted in the longitudinal direction such that the length of the unclosed part was 2 mm, 1.3 kg (dry weight) of the immobilized lipase obtained by the Preparation of immobilized enzyme (1) was packed (packing height 1300 mm), and was maintained warm at 35° C. with the jacket. A liquid prepared by mixing rapeseed oil and distilled water at a weight ratio of 10:6 was supplied from the top of the column at a rate of 4.3 kg/Hr, and a hydrolysis reaction was performed. The results are presented in Table 2. Here, the rate of degradation in the table was calculated by dividing the analytically determined acid value by the saponification value. In addition, the acid value was measured by the method described in American Oil Chemists. Society Official Method Ca 5a-40, and the saponification value was measured by the method described in American Oil Chemists. Society Official Method Cd 3a-94.

Example 2

In a column (inner diameter 200 mm, height 1500 mm) made of stainless steel equipped with a jacket, in which partition plates with slits for combination (equivalent to FIG. 4, plate thickness 2 mm, height 300 mm) having a lateral cross-section which was rectangular in shape with a size of 40 mm×40 mm (representative length 56 mm), were mounted in combination such that the length of the unclosed part was 1 mm, 11.5 kg on a dry basis of the immobilized lipase obtained by the Preparation of immobilized enzyme (1) was packed (packing height 1500 mm), and was maintained warm at 35° C. with the jacket. A liquid prepared by mixing rapeseed oil and distilled water at a weight ratio of 10:6 was supplied from the top of the column at a rate of 30 kg/Hr, and a hydrolysis reaction was performed. The results are presented in Table 2.

Comparative Example 1

A hydrolysis reaction was performed in the same procedure as in Example 1, except that partition plates were not mounted in the column made of stainless steel, and 1.4 kg on a dry basis of the immobilized lipase obtained by the Preparation of immobilized enzyme (1) was packed (inner diameter 70 mm, packing height 1300 mm). The results are presented in Table 2.

Comparative Example 2

A hydrolysis reaction was performed in the same procedure as in Example 2, except that partition plates were not mounted in the column made of stainless steel, and 12.7 kg on a dry basis of the immobilized lipase obtained by the Preparation of immobilized enzyme (1) was packed (inner diameter 200 mm, packing height 1500 mm). The results are presented in Table 2.

TABLE 2

|  | Example 1 | Example 2 | Comparative Example 1 | Comparative Example 2 |
|---|---|---|---|---|
| Representative length of lateral cross-section (mm) | 16 | 56 | — | — |
| Number of partition plates | 6 | 10 plates × 10 stages | — | — |
| Minimum distance between partition plate and inner wall of reaction column (mm) | 2 | 1 | — | — |
| Amount of packed enzyme (kg) | 1.3 | 11.5 | 1.4 | 12.7 |
| Enzyme packing porosity | 0.56 | 0.56 | 0.56 | 0.56 |
| Rate of hydrolysis (%) | 86 | 89 | 78 | 77 |
| Apparent activity of immobilized enzyme (U/g) | 710 | 830 | 377 | 354 |

From the results shown in Table 2, it was clear that when hydrolysis is performed by supplying rapeseed oil and distilled water, while partition plates are inserted into a fixed bed-type reaction column in the longitudinal direction of the fixed bed-type reaction column so as to form a plurality of tube-shaped structures, each tube having a lateral cross-section which is circular or polygonal in shape and has a representative length with at least a part being unclosed, of 100 mm or less, the rate of degradation is enhanced, and the (apparent) activity of the immobilized enzyme is effectively appeared.

Example 3

350 g (dry mass) of the immobilized enzyme A was packed (packing height 1500 mm) in a column made of stainless steel (inner diameter 35 mm, height 1600 mm) equipped with a jacket, and the column was maintained warm at 35° C. with the jacket. A liquid prepared by mixing rapeseed oil and distilled water at a mass ratio of 10:6 was supplied from the top of the column at a rate of 1.1 kg/Hr, and a hydrolysis reaction was performed. The results are presented in Table 3.

Example 4

865 g on a dry basis of the immobilized enzyme A was packed (packing height 1500 mm) in a column made of stainless steel (inner diameter 55 mm, height 1600 mm) equipped with a jacket, and the column was maintained warm at 35° C. with the jacket. A liquid prepared by mixing rapeseed oil and distilled water at a mass ratio of 10:6 was supplied from the top of the column at a rate of 2.7 kg/Hr, and a hydrolysis reaction was performed. The results are presented in Table 3.

Example 5

A hydrolysis reaction was performed by the same method as in Example 3, except that the immobilized enzyme A in Example 3 was changed to the immobilized enzyme B. The results are presented in Table 3.

Example 6

1400 g on a dry basis of the immobilized enzyme C was packed (packing height 1500 mm) in a column made of stainless steel (inner diameter 70 mm, height 1600 mm) equipped with a jacket, and the column was maintained warm at 35° C. with the jacket. A liquid prepared by mixing rapeseed oil and distilled water at a mass ratio of 10:6 was supplied from the top of the column at a rate of 4.3 kg/Hr, and a hydrolysis reaction was performed. The results are presented in Table 3.

Comparative Example 3

A hydrolysis reaction was performed by the same method as in Example 6, except that the immobilized enzyme C in Example 6 was changed to the immobilized enzyme A. The results are presented in Table 3.

Comparative Example 4

A hydrolysis reaction was performed by the same method as in Example 4, except that the immobilized enzyme A in Example 4 was changed to the immobilized enzyme B. The results are presented in Table 3.

Comparative Example 5

A hydrolysis reaction was performed by the same method as in Example 6, except that the immobilized enzyme C in Example was changed to the immobilized enzyme B. The results are presented in Table 3.

TABLE 3

|  | Example | | | | Comparative Example | | |
| --- | --- | --- | --- | --- | --- | --- | --- |
|  | 3 | 4 | 5 | 6 | 3 | 4 | 5 |
| Average particle size of immobilized enzyme (mm) (A) | 0.50 | 0.50 | 0.30 | 0.58 | 0.50 | 0.30 | 0.30 |
| Column diameter of fixed bed-type reaction column (mm) (B) | 35 | 55 | 35 | 70 | 70 | 55 | 70 |
| (B)/(A) | 70 | 110 | 117 | 121 | 140 | 183 | 233 |
| Rate of hydrolysis (%) | 88 | 87 | 90 | 87 | 73 | 82 | 74 |
| Apparent activity of immobilized enzyme (U/g) | 850 | 800 | 1026 | 739 | 248 | 408 | 268 |

From the results shown in Table 3, it was clear that, also in the case of using a fixed bed-type reaction column having a column diameter of 35 mm or larger, when the immobilized enzyme is packed inside the reaction column such that the ratio of the column diameter to the average particle size of the immobilized enzyme (column diameter/average particle size) is 135 or less, the rate of degradation is enhanced, and the (apparent) activity of the immobilized enzyme is effectively appeared.

The invention claimed is:

1. A process for producing fatty acids, comprising
feeding a liquid mixture comprising two liquid phases formed of an oil-phase substrate containing oils and fats and an aqueous phase substrate into a fixed-bed reaction column comprising an immobilized lipase, and
allowing the two liquid phases to flow in a co-current manner wherein a hydrolysis reaction is performed when said liquid phases are in contact with said immobilized lipase in said fixed-bed reaction column;
wherein the fixed-bed reaction column comprises partition plates so as to comprise a plurality of tube-shaped structures,
wherein each tube-shaped structure has a cross-section which is rectangular, circular, oval, or polygonal in shape with at least a part being unclosed and the cross-section has a representative length of 100 mm or less;
wherein the representative length means a length of the diagonal if the cross-section is rectangular,
wherein the representative length means a length of the diameter if the cross-section is circular,
wherein the representative length means a length of the diameter of a circle having the same area as projected area of the shape if the cross-section is oval or polygonal shape, and
wherein the length of the part being unclosed in the cross-section is 0.1 to 10 mm.

2. The process according to claim 1, wherein the partition plates are divided into multiple stages in the vertical direction.

3. The process according to claim 1, wherein the partition plates are divided into multiple parts in the lateral direction.

4. The process according to claim 1, wherein said fixed-bed reaction column comprises a gap between the partition plates and the inner wall of the fixed-bed reaction column, wherein the narrowest part of said gap is 1 mm or larger.

5. The process according to claim 1, wherein said oil phase substrate is at least one selected from the group consisting of a plant oil, an animal oil, and a mixture of an oil and a fat.

6. The process according to claim 5, wherein said oil phase substrate further comprises at least one of a triacylglycerol, a diacylglycerol, a monoacylglycerol or fatty acid.

7. The process according to claim 1, wherein said oil phase substrate is at least one selected from the group consisting of rapeseed oil, soybean oil, sunflower oil, palm oil linseed oil, beef tallow, pork fat, and fish oil.

8. The process according to claim 1, wherein said aqueous phase substrate is at least one selected from the group consisting of water and water containing a water-soluble component mixed therein.

* * * * *